(12) United States Patent
Kim et al.

(10) Patent No.: US 9,368,667 B1
(45) Date of Patent: Jun. 14, 2016

(54) PLASMON FIELD EFFECT TRANSISTOR

(71) Applicants: Sung Jin Kim, Miami, FL (US); Juhyung Yun, Buffalo, NY (US)

(72) Inventors: Sung Jin Kim, Miami, FL (US); Juhyung Yun, Buffalo, NY (US)

(73) Assignee: Sung Jin Kim, Miami, FL (US)

( * ) Notice: Subject to any disclaimer, the term of this patent is extended or adjusted under 35 U.S.C. 154(b) by 78 days.

(21) Appl. No.: 14/171,342

(22) Filed: Feb. 3, 2014

Related U.S. Application Data

(60) Provisional application No. 61/759,595, filed on Feb. 1, 2013.

(51) Int. Cl.
  *H01L 31/062* (2012.01)
  *H01L 31/113* (2006.01)
  *H01L 31/0352* (2006.01)

(52) U.S. Cl.
  CPC .... *H01L 31/1136* (2013.01); *H01L 31/035272* (2013.01)

(58) Field of Classification Search
  USPC .......... 136/256; 257/13, 290; 324/95
  See application file for complete search history.

(56) References Cited

U.S. PATENT DOCUMENTS

| | | |
|---|---|---|
| 2009/0243589 A1 | 10/2009 | Blumberg |
| 2010/0147674 A1* | 6/2010 | Krivoshlykov ............ 204/157.4 |
| 2015/0122320 A1* | 5/2015 | Wu et al. ........................ 136/256 |

OTHER PUBLICATIONS

Knight et al.,"Photodetection with Active Optical Antennas," Science, pp. 702-704, dated May 6, 2011, vol. 332, consisting of 4-pages.
Lee et al., "Surface Plasmon-Driven Hot Electron Flow Probed with Metal-Semiconductor Nanodiodes," ACS Publications, NANO Letters, vol. 11, Issue 10, pp. 4251-4255, dated Sep. 14, 2011, consisting of 5-pages.
Wang et al., "Plasmonic Energy Collection through Hot Carrier Extraction," ACS Publications, NANO Letters, vol. 11, Issue 12, pp. 5426-5430, dated Oct. 24, 2011, consisting of 5-pages.
Sobhani et al., "Narrowband photodetection in the near-infrared with a plasmon-induced hot electron device," Nature Communications, vol. 4, Article 1643, dated Mar. 27, 2013, consisting of 6-pages.
Lin et al., "Plasmonic enhancement of photocurrent in MoS2 field-effect-transistor," AIP Applied Physics Letters, vol. 102, dated May 21, 2013, consisting of 4-pages.

* cited by examiner

*Primary Examiner* — Errol Fernandes
(74) *Attorney, Agent, or Firm* — Christopher & Weisberg, P.A.

(57) ABSTRACT

A field effect transistor (FET) is provided. The FET includes a first material layer, second material layer and a third material layer. The third material layer includes an n-type silicon substrate layer and a gate electrode. The gate electrode includes an insulating substrate with at least one conducting metal. The second material layer is disposed on the third material layer. The first material layer is disposed on the second material layer. A source electrode is disposed on the first material layer. A drain electrode is disposed on the first material layer. A plurality of gold nanostructures are disposed on an active channel of the FET. The plurality of gold nanostructures are electrically isolated from the source electrode, drain electrode and gate electrode. The plurality of gold nanostructures contribute to a drain current of the FET based at least in part on plasmonic absorption of photons.

20 Claims, 24 Drawing Sheets

PLASMON FIELD EFFECT TRANSISTOR

CROSS-REFERENCE TO RELATED APPLICATION

This application is related to and claims priority to U.S. Provisional Patent Application No. 61/759,595, filed Feb. 1, 2013, entitled PLASMON FIELD EFFECT TRANSISTOR, the entirety of which is incorporated herein by reference.

FIELD OF THE INVENTION

The present invention relates to a method, device and system for detecting electromagnetic energy, and in particular for detecting electromagnetic energy with a plasmon Field Effect Transistor.

BACKGROUND OF THE INVENTION

The interests on plasmons, associated with nanostructured metals, have remarkably increased in the past decade. Surface plasmon resonance (SPR) sensor is one of the successful applications, which is widely used in biomedical research. On the other hand, localized surface plasmon resonance (LSPR) is also widely studied in a broad range of applications. The distinct property of LSPR is a tailored and sharp absorption and scattering peaks depending on the shape and sizes of the metal nanostructures. LSPR technology also possesses a more superior thermal stability than SPR technology. Therefore, LSPR absorption is very stable in the range of room temperature to 200° C.

While the mechanisms of LSPR and SPR seem comparable, the fundamentals of these two technologies are quite different. SPR uses a two-dimensional metal nanostructure to create strong plasmon polariton, which propagates on the metal surface in an evanescent mode. SPR technology requires a special optical geometry and control to achieve highly sensitive detection. In contrast, LSPR occurs when the metal structure (0-dimensional structure) is much smaller than the wavelength of the light. There is a specific energy (i.e. wavelength) that makes the electrons in the metal resonate by absorbing the photon energy. Therefore, it appears with a strong absorption at specific wavelength and that the absorbance is sensitive to the refractive indices of the host matrix and the metal nanostructure.

Some existing technologies use plasmon induced hot electron detection using photodetector structures. The absorbed photons in metal nanostructure create "hot" electron-hole pairs which have high enough energy to be extracted through Schottky barrier. For example, as illustrated in FIG. 1, a nanoparticle based semiconductor 8 is illustrated. Semiconductor 8 includes nanostructures 6 and electrodes 4.

Semiconductor 8 uses a Schottky junction based on internal hot-electron emission to provide a photocurrent. In particular, the photons that are absorbed in a metal contribute to generating "hot electrons" and, if the hot electron energy is high enough, the hot electrons can overcome the Schottky energy barrier at the boundary between metal and semiconductor. Therefore, the hot electrons move to the semiconductor, resulting in photocurrent.

However, semiconductor 8 relies on making the nanostructures serve as one of the electrodes in a diode structure such that the electrical connection to the device is maintained. Semiconductor 8 and other similar existing technologies exhibit very low responsivity (A/W) or external quantum efficiency due to limited absorption in the thin metal structure and inefficient hot electron diffusion from metal to semiconductor. Another issue with semiconductor 8 and these existing technologies is that the Schottky barrier height severely limits the minimum amount of detectable light energy.

Further, surface plasmon based sensors are successfully used in various applications, since this optical phenomenon provides extreme sensitivity and robustness. Conventional SPR sensors consist of a thin metal surface or nanoparticle structure, excitation light source and detectors with controlled optical geometry. However, since conventional SPR sensors use multiple components and long optical path for better resolution, it is difficult to have multiplexing capability in a lab-on-a-chip device which has excitation source, detector and sensing elements all together.

SUMMARY OF THE INVENTION

The present invention advantageously provides a method and system for detecting electromagnetic energy with a plasmon Field Effect Transistor.

A field effect transistor (FET) is provided. The FET includes a first material layer, a source electrode disposed on the first material layer and a drain electrode disposed on the first material layer. The FET further includes a dielectric layer adjacent to a surface of the first material layer and a gate electrode in physical contact with the dielectric layer. The FET further includes a plurality of nanostructures disposed on the first material layer and being electrically isolated from both the source electrode and drain electrode. The plurality of nanostructures are configured to affect a drain current of the FET based at least in part on plasmonic absorption of photons.

A sensor device is provided. The sensor device includes a first material layer, a source electrode disposed on the first material layer and a drain electrode disposed on the first material layer. The sensor device further includes a dielectric layer adjacent to a surface of the first material layer and a gate electrode in physical contact with the dielectric layer. The sensor device includes a plurality of nanostructures disposed on the first material layer and being electrically isolated from both the source electrode and drain electrode. The plurality of nanostructures are configured to affect a drain current of the FET based at least in part on plasmonic absorption of photons. The sensor device further includes a current detector. The current detector is configured to detect an increase in the drain current of the FET when light of at least one wavelength is incident on the plurality of nanostructures. At least one bias voltage of the source electrode and drain electrode remains unchanged during the detected increase of the drain current.

A field effect transistor (FET) is provided. The FET includes a first material layer. The first material layer includes one of Si layer, semiconducting metal oxide layer, group III-V compound semiconductor layer, Group II-VI compound semiconductor layer and group III-nitride semiconductor layer. The FET includes a second material layer such as an insulating dielectric layer. The second material layer includes one of a Silicon Dioxide ($SiO_2$) layer Aluminum Oxide ($Al_2O_3$) layer and Silicon Nitride (SiNx) layer. The FET includes a third material layer. The third material layer includes a n-type silicon substrate layer and an insulating layer with conducting metal acting as a gate electrode. The second material layer is disposed on the third material layer. The first material layer is disposed on the second material layer. A source electrode is disposed on the first material layer. A drain electrode is disposed on the first material layer. A gate electrode is disposed on the third material layer. A plurality of gold nanostructures are disposed on an active channel of the FET. The plurality of gold nanostructures are electrically isolated from the source electrode, drain electrode and gate electrode. The plurality of gold nanostructures are configured to contribute to a drain current of the FET based at least in part on plasmonic absorption of photons.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
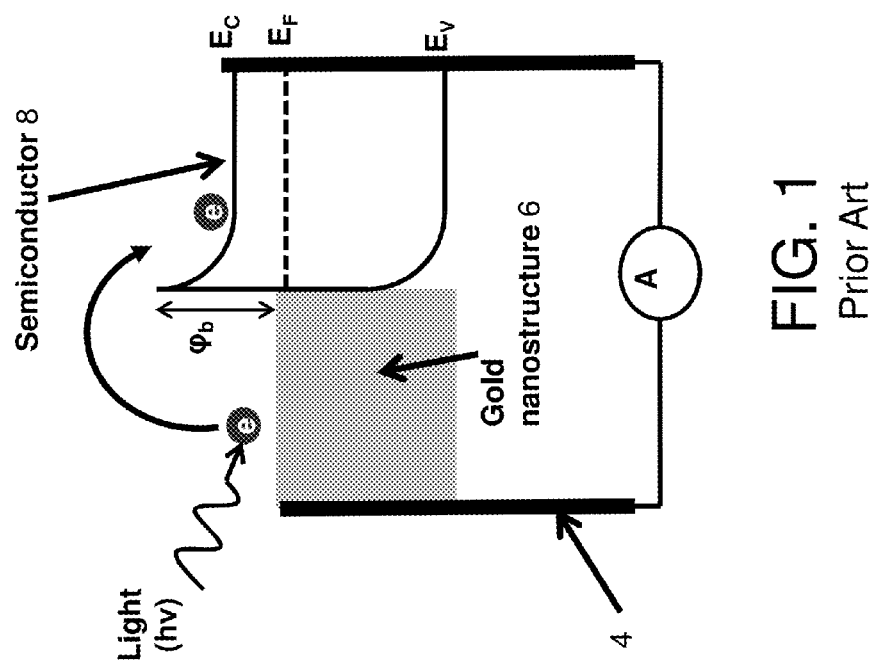
FIG. 1 illustrates an existing nanostructure based Schottky junction detector.

The present invention advantageously provides a method, device and system for detecting electromagnetic energy, and in particular for detecting electromagnetic energy with a plasmon Field Effect Transistor. Accordingly, the system and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Figure 2:
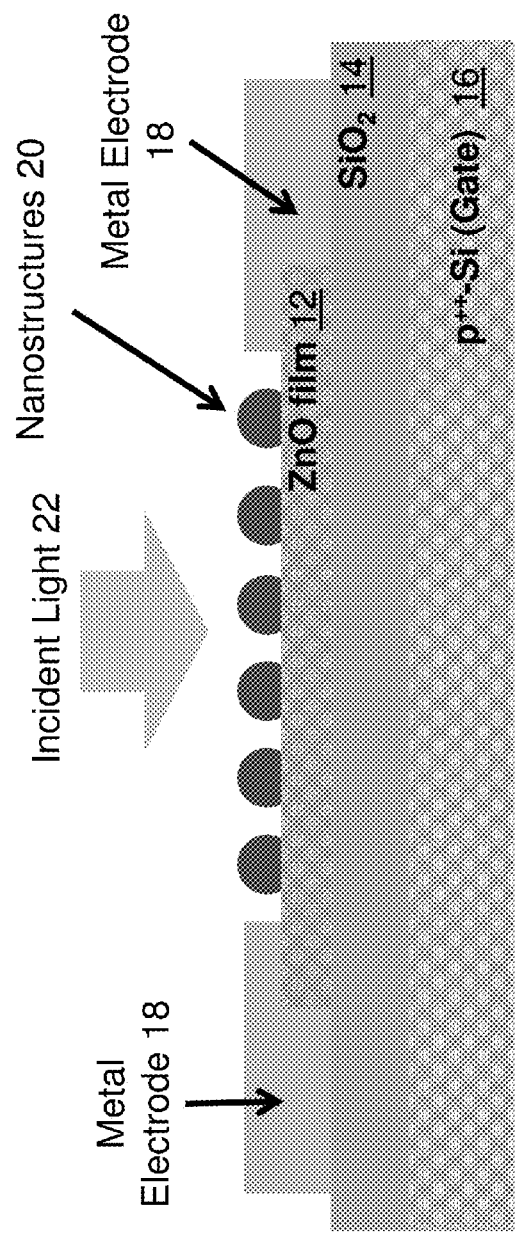
FIG. 2 illustrates an exemplary plasmon Field Effect Transistor (FET) in accordance with the principles of the present invention.

Referring now to the drawing figures in which like reference designators refer to like elements there is shown in FIG. 2 an exemplary plasmon Field Effect Transistor (FET) in accordance with the principles of the present invention and designated generally as "10." FET 10 may be based on any semiconducting materials and may include organic and inorganic, N and P types. FET 10 includes a first material(s) or composite layer 12 (hereinafter first material layer 12) that may be an n-type zinc oxide (ZnO) film that provides a wide bandgap semiconductor channel (<3 eV). ZnO is a wide bandgap semiconducting material (Eg—3.25 eV, 380 nm UV) that is transparent in visible light. First material layer 12 of FET 10 is not limited to ZnO and may alternatively use GaN or $TiO_2$, Si, semiconducting metal oxide, group III-V compound semiconductor, Group II-VI compound semiconductor and group III-nitride semiconductor, among other wideband gap semiconductors. First material layer 12 may be from 10 nm to 100 nm thick, among other thicknesses, depending on design need. The wide bandgap material of the first material layer 12, e.g., ZnO, GaN, or TiO2, does not, by itself, have an optical response from visible to infrared spectral range. Therefore, FET 10 without metal nanostructures 20 will not have any response from light illumination below their energy bandgap.

FET 10 may further include a second material(s) or composite layer 14 (hereinafter second material layer 14) that may be a Silicon Dioxide ($SiO_2$) insulating layer or an insulating (dielectric) layer of another material or compound. Second material layer 14 may be from 10 nm to 300 nm thick. FET 10 may further include a third material layer 16 such as a heavily doped n-type silicon substrate or layer of other conductive materials. The third material(s) or composite layer 16 (hereinafter third material layer 16) may include a highly doped n-type silicon layer, and an insulating layer with conducting metal that act as the gate electrode of FET 10. First material layer 12 may be disposed on second material layer 14. Second material layer 14 may be disposed on third material layer 16. First, second and third material layers may include one or more periodic elements, respectively.

FET 10 may further include one or more electrodes 18 such as chromium (Cr) and/or gold (Au) electrodes. For example, FET 10 may include a drain electrode, source electrode and gate electrode. Electrodes 18 are disposed on at least on first and second material layers. One or more bias voltages may be applied to electrodes 18, as discussed in detail below. In one embodiment, third material layer 16 includes Gate electrode 18 that is in physically contact, adjacent and/or connected to the dielectric layer.

FET 10 further includes one or more metal nanostructures 20 disposed on first material layer 12 and/or active channel of FET 10, i.e., a plurality of nanostructures 20 are disposed on the first material layer and are electrically isolated from both the source electrode and drain electrode. Metal nanostructures 20 are electrically isolated from electrodes 18, i.e., from drain, source and gate of FET 10; therefore, metal nanoparticles 20 are free from voltage bias when FET 10 is operating. The electrical isolation of metal nanostructures 20 allows for the metal nanoparticles to be designed in various shapes with a varied selection of the refractive index of surrounding materials.

Nanostructures may be any plasmonic structures that exhibit plasmonic absorption from UV to THz range. For example, nanostructures may include nonparticles, nanoholes, nanorods, grating, slit structures and two dimensional metal films, among others. Nanostructures 20 may be gold nanoparticles that exhibit a strong absorption by the localized surface plasmon resonance in visible color. Alternatively, metal nanostructures 20 can be structures or particles made from Au, Ag or Cu that is disposed in the active area/channel of FET 10. The plurality of nanostructures are configured to affect a drain current of the FET based at least in part on plasmonic absorption of photons. Gold nanoparticles 20 have a plasmon effect starting green color light. If the nanoparticle is in aqueous solution, typically it has a strong absorption around 514 nm wavelength (green color) and shows pink color. This strong absorption varies depending on the host materials surrounding gold nanoparticles. If the higher refractive materials surrounded on the gold nanoparticles, the absorption peak shifts to red color (longer wavelength) and shows blue color.

Nanostructures 20 and first material layer 12 form a Schottky junction as will be described in detail with respect to FIG. 3. Without nanostructures 20, FET 10 would ideally have no optical response under visible light illumination. The metal nanoparticles have strong plasmonic absorption spectrum depending on the refractive index of materials surrounding nanostructures 20.

Figure 3:
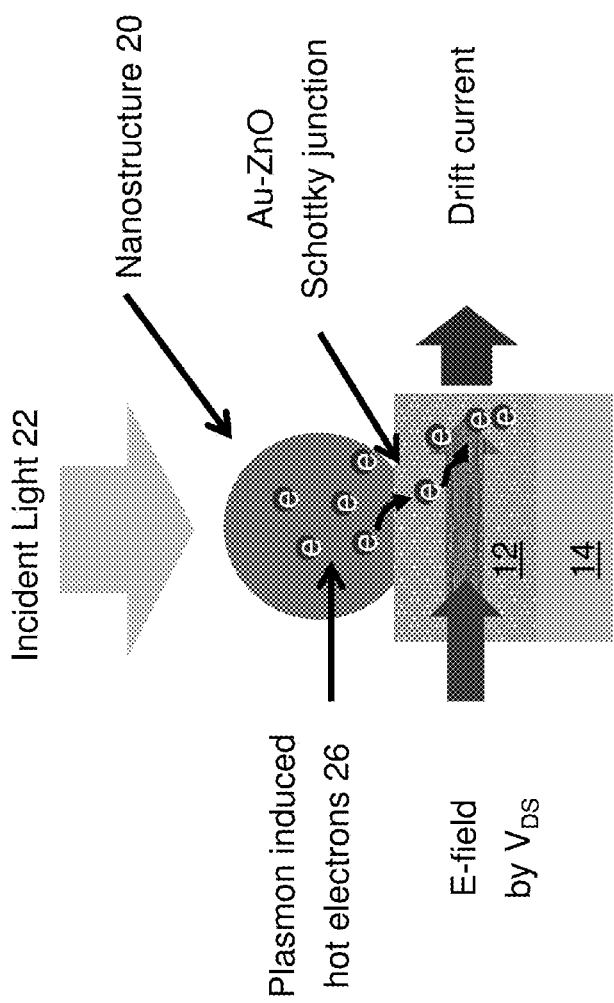
FIG. 3 illustrates the plasmon induced hot electron extraction process at Schottky Junction of the FET in accordance with the principles of the present invention.

FIG. 3 illustrates the plasmon induced hot electron extraction process at Schottky Junction 24 of FET 10. In particular, incident light 22, i.e., photons, are absorbed by metal nanostructure 20, thereby inducing/generating hot electrons 26. Hot electrons 26 with higher energy than the Schottky barrier, e.g., 0.5 eV, may overcome the Schottky barrier to move from metal nanostructure 20 to first material layer 12 by the Fowler theory. In one example, since the photon energy of visible spectrum is greater than 1.7 eV, the absorbed photons will migrate from metal nanoparticles 20 to first material layer 12. Hot electrons 26 that have moved to first material layer 12 supply more electrons (charge) to the first material layer, e.g., ZnO channel, resulting in increased drift current, i.e., plasmon induced hot electrons contribute to the drift current of FET 10. The current may be detected by a current detector and/or other measurement device for further processing in order to determine whether an amount of plasmon induced hot electrons 26.

Figure 4:
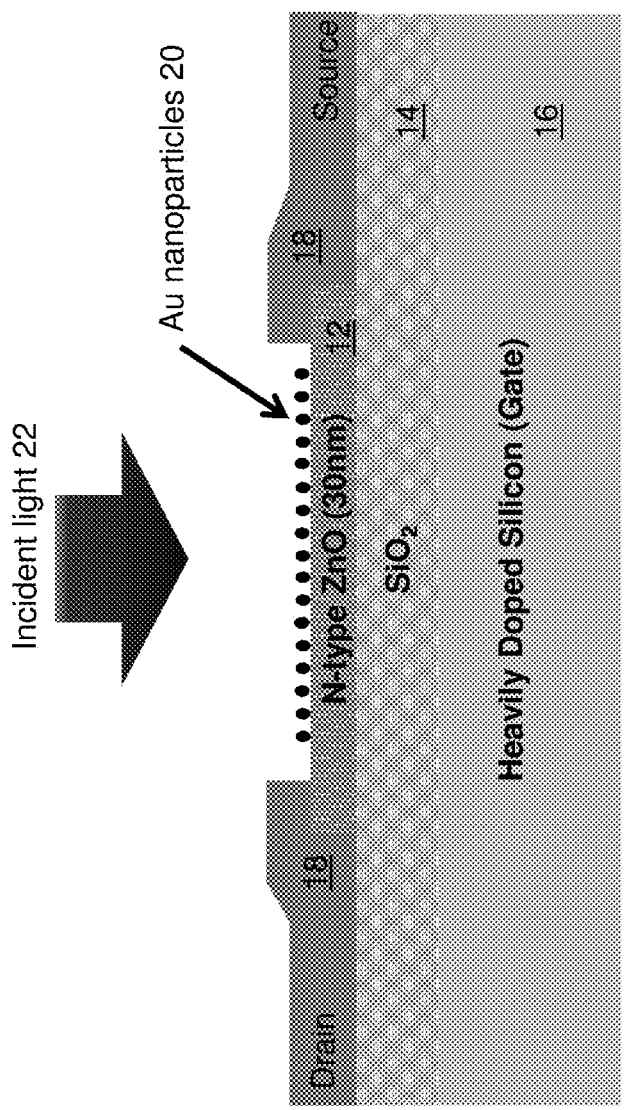
FIG. 4 illustrates another embodiment of the FET in accordance with the principles of the present invention.

FIG. 4 illustrates another embodiment of FET 10. In particular, FET 10 includes a drain, source and gate. First material layer 12 is a N-type ZnO layer having a thickness of 30 nm. Second material layer 14 is a $SiO_2$ layer and third material layer a heavily doped Silicon layer/gate. Nanostructures 20 are gold nanoparticles that are disposed only on the active channel of FET 10. Similar to FIG. 3, plasmon induced hot electrons move from gold nanoparticles 20 to the N-type ZnO layer, thereby supplying more electrons (charge) to the ZnO layer, resulting in increased Drain current (Id). The drain current of FET 10 reflects directly the light energy absorbed by metal nanoparticles 20, i.e., plasmon induced hot electrons 26 contribute to the drain current. Further, one or more voltage biases applied to the source, drain and/or gate advantageously allows the modification of the Schottky barrier of Schottky junction 24, which changes the detection properties of FET 10.

Figure 5:
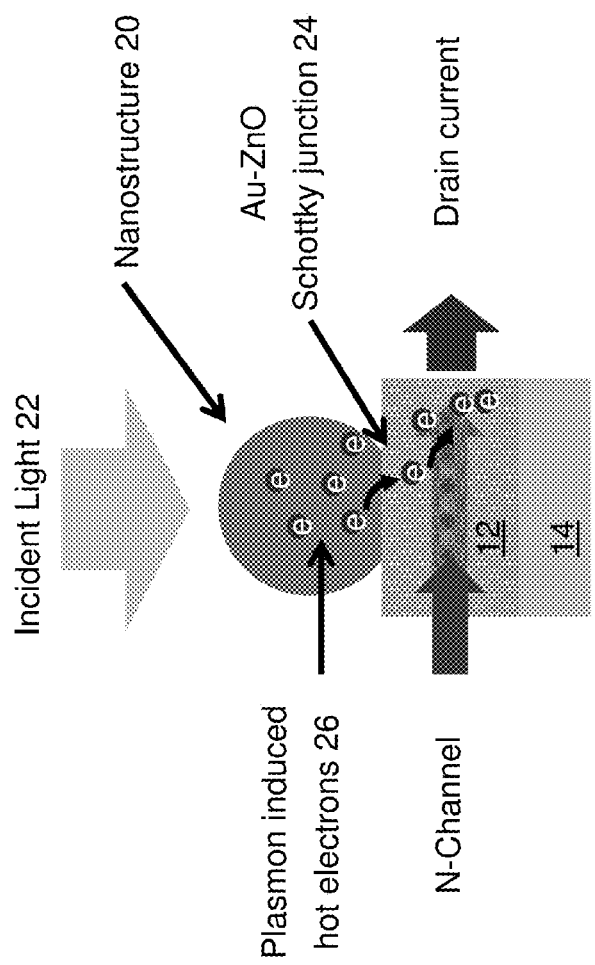
FIG. 5 illustrates the plasmon induced hot electron extraction process at Schottky Junction of the FET in accordance with the principles of the present invention.

FIG. 5 illustrates the plasmon induced hot electron extraction process at Schottky Junction 24 of FET 10. FET 10 may have a voltage bias across Drain and Source electrodes 18 with an additional control voltage bias across Gate and Source electrodes 18. When FET 10 is in a normal operating condition there is current through Drain to Source which is called as drain current. The metal nanoparticles 20 on the semiconductor channel area of FET 10 are electrically isolated when they are in normal operating condition and create metal-semiconductor Schottky junction, as discussed above.

Figure 6:
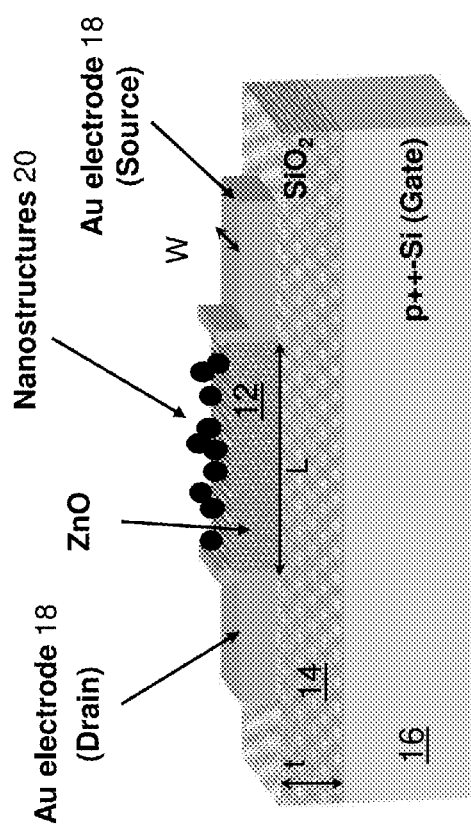
FIG. 6 illustrates a perspective view of the FET of FIG. 5 in accordance with the principles of the present invention.
Figure 8:
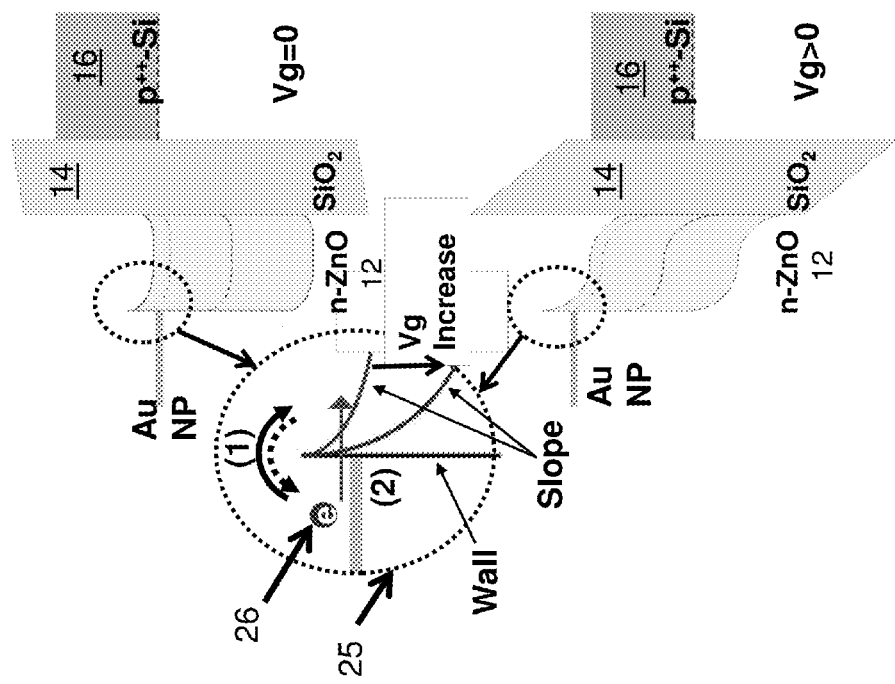
FIG. 8 illustrates the energy band structure of the FET in accordance with the principles of the present invention.

FIG. 6 illustrates a perspective view of FET 10 of FIG. 4 where W denotes channel width, t denotes first material layer thickness and L denotes channel length. Channel length, L, may vary from 0.1-1000 micrometers, channel width can vary from 0.1-1000 micrometers and first material layer thickness can vary from 10 to 300 nanometers. The migrated electrons in the ZnO can be extracted by mainly two mechanisms. First, the gate voltage bias creates a channel to move out these photo induced hot electronics with strong drift field across drain and source as shown in FIG. 8. With no gate voltage, the plasmon induced hot electrons are in an equilibrium condition. Therefore, the hot electrons can migrate by only a thermionic diffusion mechanism (1). Also, the positive gate bias, i.e., Vg>0, will reform the energy band structure as shown in FIG. 8, discussed in detail below. Consequently, the narrowed Schottky barrier will allow increased electron tunneling (2) thorough the Schottky barrier. And it creates electric field to the channel region. Thus, these processes will facilitate more electrons move over to the ZnO channel, resulting increased Drain current (Id). The plasmonic absorption of nanoparticle can be tailored by the size or shape of nanoparticles, and the refractive index surrounding the nanostructures 20. Since the spectral response of the drain current should be matched with the absorption spectrum of gold nanostructures 20, the spectral response of the plasmon FET can be easily tuned.

Figure 7:
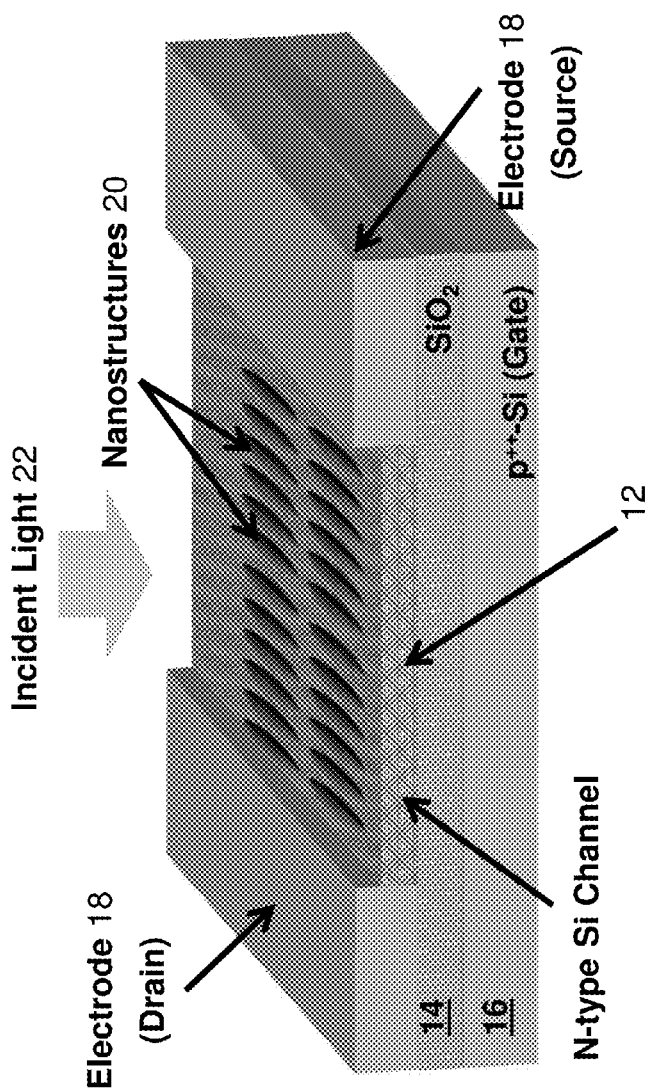
FIG. 7 illustrates another embodiment of the FET in accordance with the principles of the present invention.

FIG. 7 illustrates another embodiment of FET 10 in which nanostructures 20 have a different shape from nanostructures of FIG. 2, thereby changing the optical properties of FET 10. Similar to FIGS. 2-6, nanostructures 20 remain electrically isolated from electrodes 18. FIG. 8 illustrates the energy band structure of FET 10, e.g., Au—ZnO plasmon FET. In particular, Schottky barrier 25 may be modified by Gate voltage bias and two hot electron migration processes, i.e., thermionic diffusion (1) and tunneling (2). Thermionic diffusion (1) occurs if hot electron 26's energy is higher than the Schottky barrier height such that hot electron 26 will diffuse to the semiconductor layer and reach an equilibrium condition. The plasmon induced hot electrons 26 are in an equilibrium condition when Vg=0 such that hot electrons 26 can only migrate by the thermionic diffusion mechanism (1).

Tunneling (2) refers to quantum tunneling that occurs through a thin semiconductor wall. When the gate of FET 10 is biased, the energy band from metal nanostructures 20 to gate electrode 18 will be modified with potential slope as illustrated in FIG. 8. The higher the Vg, the greater the slope, which reduces the Schottky barrier height. In other words, the internal field created by gate bias facilitates electrons to move to the other boundary where FET 10 channel is located. Then, migrated hot electrons 26 contribute to increase the channel size, i.e., conductivity, such as to allow more drain current to flow. Therefore, the collected current from FET 10 directly reflects the plasmonic absorption from the nanostructures 20, but is not limited to the number of hot electrons generated by the nanostructures 20. The semiconductor wall at the Schottky junction becomes thinner and facilitates electron migration via the quantum tunneling processes.

Figure 9:
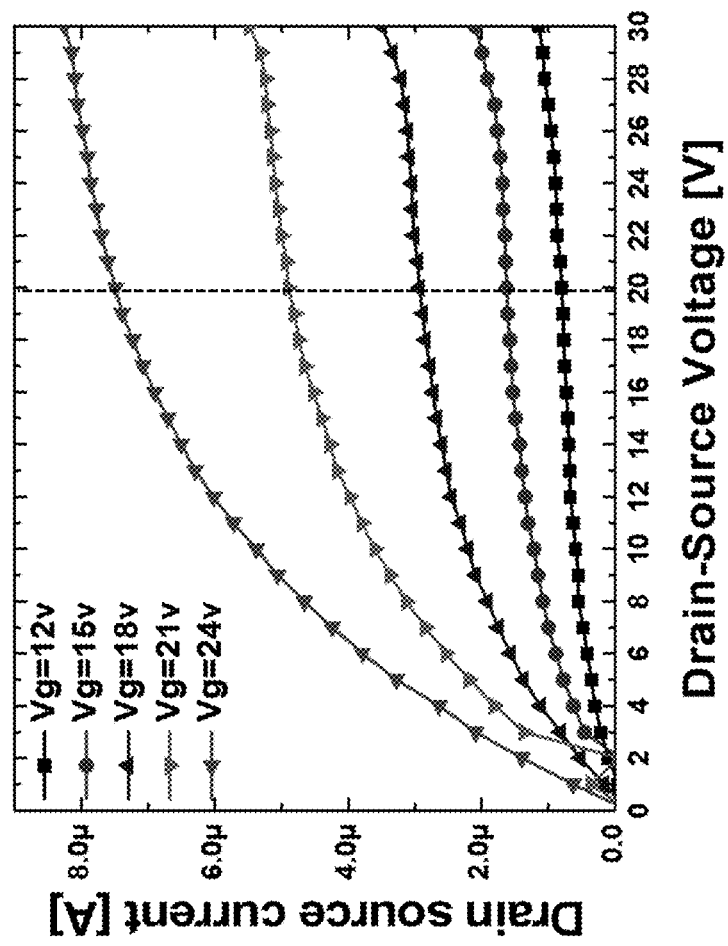
FIG. 9 illustrates drain current FET characteristic curves under various gate voltage bias in accordance with the principles of the present invention.
Figures 10, 11:
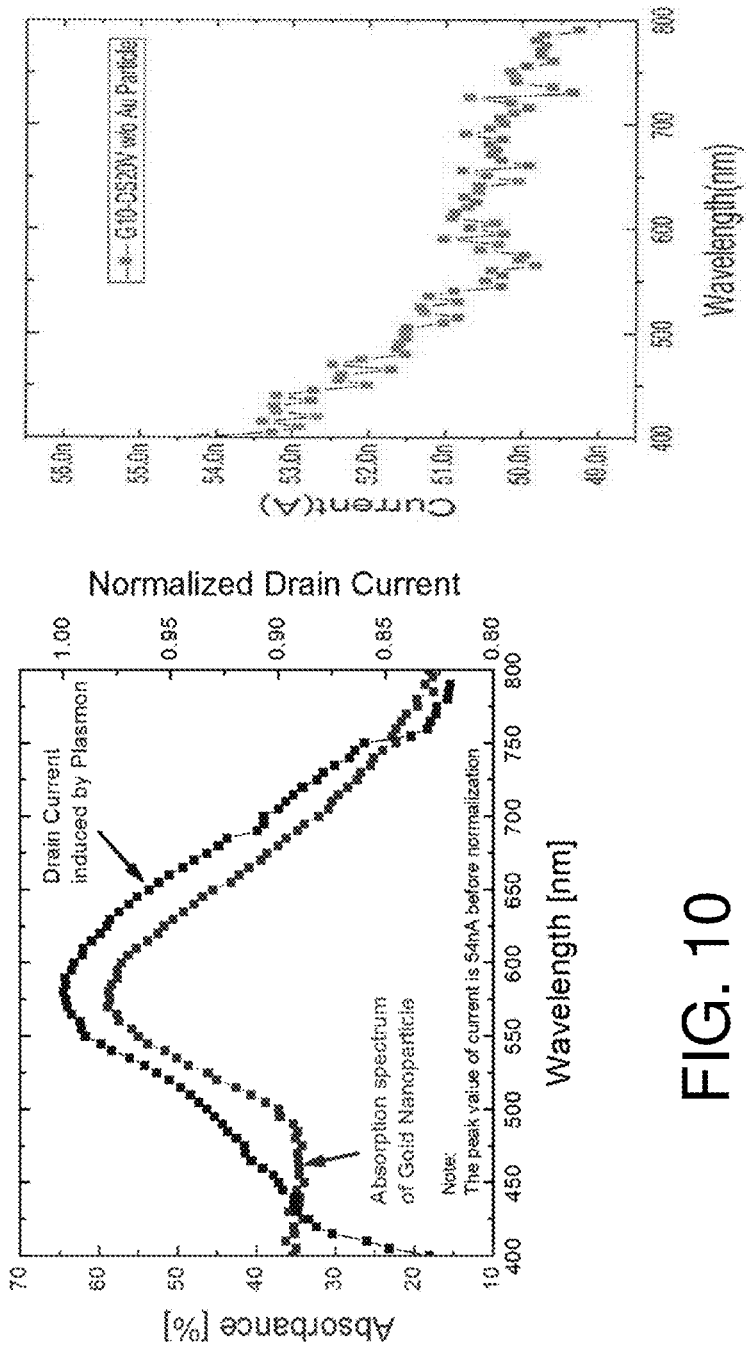
FIG. 10 illustrates the absorptions spectrum of gold nanoparticles and drain current of FET with gold nanoparticles in accordance with the principles of the present invention.
FIG. 11 illustrates the spectral response of drain current from a reference sample without gold nanoparticle in accordance with the principles of the present invention.
Figure 12:
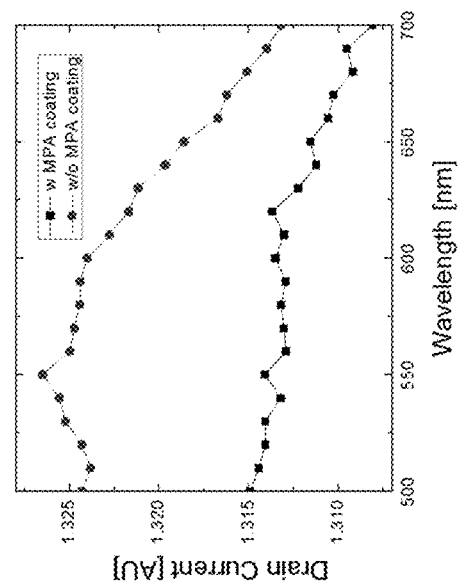
FIG. 12 illustrates the absorbance of gold nanoparticle on a glass substrate with and without MPA (mercaptopropionic acid) treatment in accordance with the principles of the present invention.

FIG. 9 illustrates drain current FET 10 characteristic curves under various gate voltage bias. In this embodiment, W/L=100 μm/100 μm. FIG. 10 illustrates the absorptions spectrum of gold nanoparticles 20. FIG. 11 illustrates the spectral response of drain current from a reference sample without gold nanoparticle such that there is plasmonic induced current. FIG. 12 illustrates the absorbance of gold nanoparticle on the glass substrate with and without MPA (mercaptopropionic acid) treatment. MPA increases the refractive index surrounding the gold nanoparticle such that the plasmonic absorbance shifts to longer wavelength.

Figure 13:
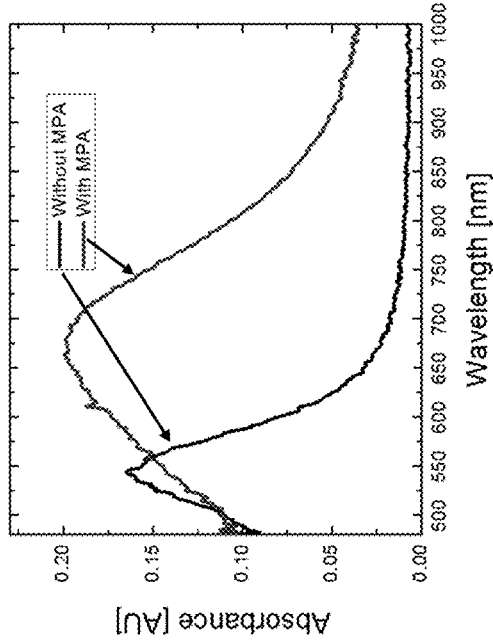
FIG. 13 illustrates the spectral response of the Drain current (Id) with and without MPA coated gold nanoparticle in accordance with the principles of the present invention.
Figure 14:
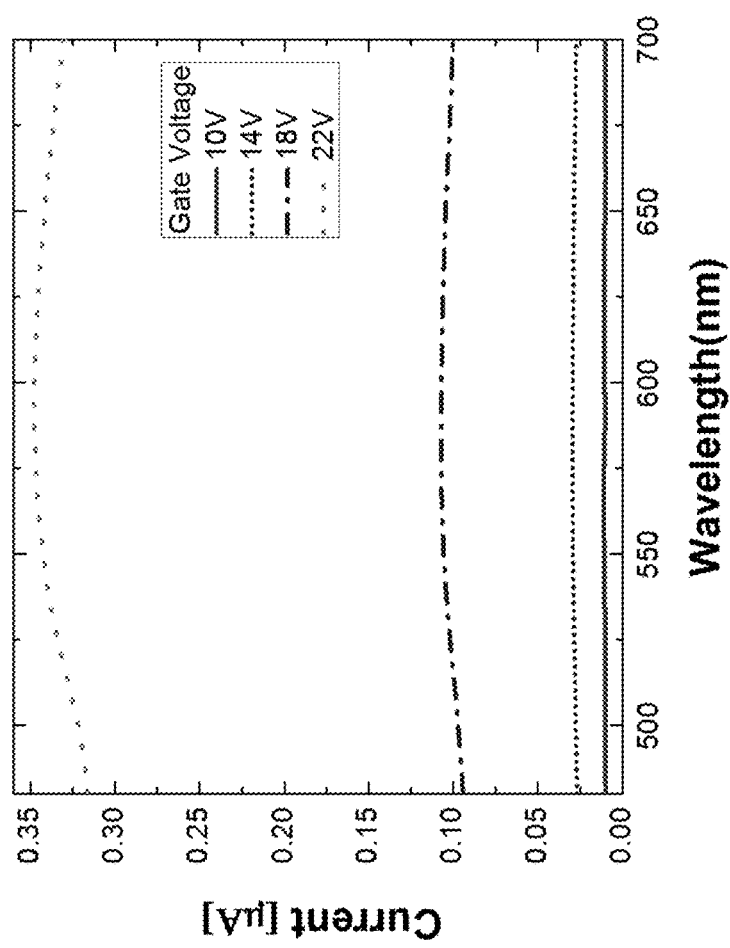
FIG. 14 illustrates the plasmon induced drain current under different Gate bias condition in accordance with the principles of the present invention.

FIG. 13 illustrates the spectral response of the Drain current (Id) with and without MPA coated gold nanoparticle. Further, FIG. 13 illustrates there is plasmonic induced drain current matched with the absorbance of gold nanoparticle shown in FIG. 12. FIG. 14 illustrates the drain current output with different gate voltage bias. The gate voltage bias controls the energy barrier between nanostructure 20 and first material layer 12, e.g., ZnO. The plasmonic induced current increases with higher gate voltage bias. FIG. 14 shows the plasma induced drain current under different Gate bias condition. Drain current is dependent on gate bias due to the controlled energy barrier height. Drain current dependence on gate bias is also illustrated and discussed in detail with respect to FIG. 15 below.

Figure 15:
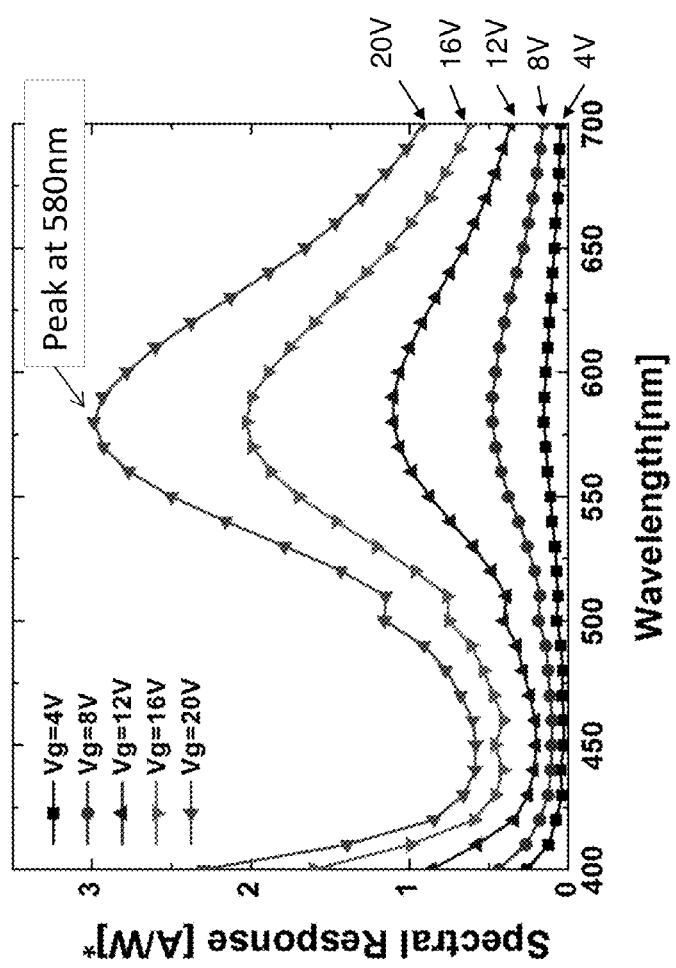
FIG. 15 illustrates the drain current output with different gate voltage bias in accordance with the principles of the present invention.

FIG. 15 illustrates the drain current output with different gate voltage bias. The gate voltage bias controls the energy barrier between nanostructure 20 and first material layer 12, e.g., ZnO. The plasmonic induced current is increased with higher gate voltage bias. FIG. 15 shows that the gate voltage controls the current from plasmonic absorption by modifying the energy barrier, i.e., increased gate voltage reduces the energy barrier. Under 20V of gate bias, the spectral response value R (A/W) reached more than 3, which indicates there is an efficient amplification process involved depending on the gate voltage bias condition. Therefore, FET 10 facilitates hot electron emission by forming the channel and by controlling the Schottky barrier width, thereby enabling highly sensitive detection of plasmonic energy. This amplification is explained by the energy band model described in FIG. 8.

Figure 16:
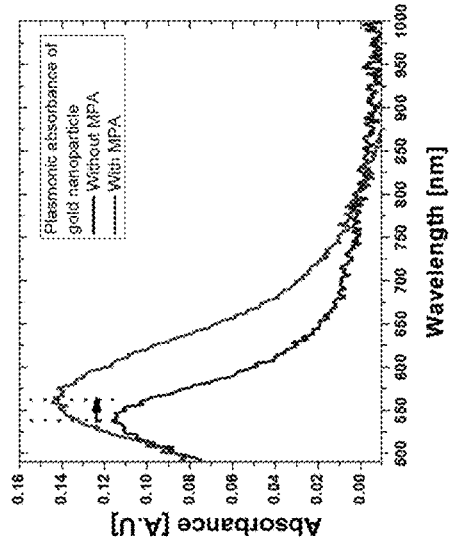
FIG. 16 illustrates the absorbance of gold nanoparticle on the glass substrate with and without MPA treatment in accordance with the principles of the present invention.

FIG. 16 illustrates the plasmonic absorbance of gold nanoparticle 20 on a glass substrate which is identically fabricated on the FET 10 channel. FET 10 produced a current response substantially the same as the absorption spectrum of gold nanoparticles under voltage biased condition. The refractive index surrounding the gold nanoparticles 20 was varied using Mercaptopropionic Acid (MPA). MPA has the refractive index around 1.5 and good binding property on the gold surface due to the thiol (—SH) terminated structure. Because the MPA coated gold nanoparticle increases the average refractive index, it makes a red shift of the peak of plasmonic absorption spectrum. FIG. 16 shows the absorbance of gold nanoparticle on the glass substrate with and without MPA treatment. MPA increases the refractive index surrounding gold nanoparticles 20 and shifts its plasmonic absorbance to longer wavelength.

Figure 17:
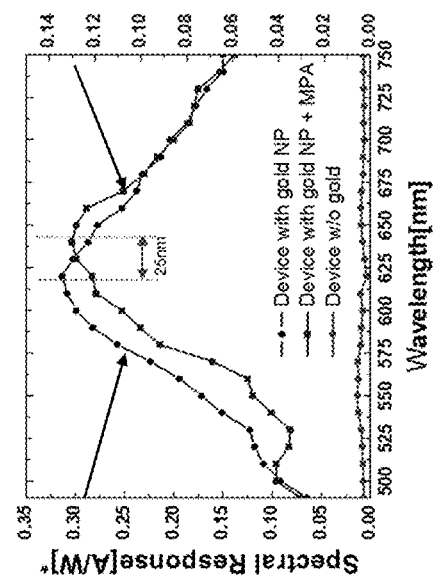
FIG. 17 illustrates the spectral response of a FET without gold nanoparticles, with gold nanoparticles and with gold nanoparticles+MPA in accordance with the principles of the present invention.

FIG. 17 illustrates the spectral response of a FET without gold nanoparticles 20, FET 10 with gold nanoparticles 20 and FET 10 with gold nanoparticles+MPA. FET without gold nanoparticles 20 did not produce any current from plasmonic absorption, while FET 10 with gold nanoparticles has a well matched spectral response with plasmonic absorption of gold nanoparticles 20. The discrepancy of the wavelength of the absorption peaks between FIG. 16 and FIG. 17 is due to the difference of refractive indices.

Figure 18:
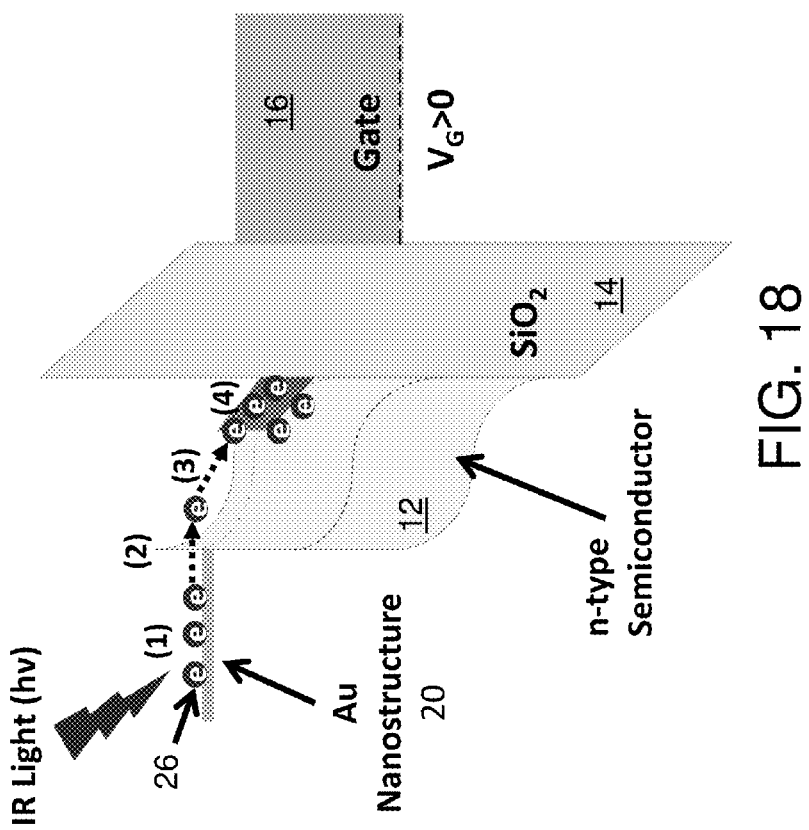
FIG. 18 illustrates Plasmon energy detection and amplification process in the FET in accordance with the principles of the present invention.

FIG. 18 illustrates Plasmon energy detection and amplification process in FET 10. The energy band diagram represent the cross section of gold nanostructure 20 to gate of FET 10. Under positive gate voltage bias, the energy band of the n-type semiconductor, i.e., first material layer, will have an internal electric field that forces accumulation of hot electrons 26 in the channel of FET 10. Also, the Schottky barrier become thin enough to make easy tunneling of hot electrons 26. The numbered processes mean: (1): infrared (IR) absorption in gold nanostructure 20, (2): hot electron 26 tunneling through the thin Schottky barrier, (3): internal field assisted hot electron drift, and (4): hot electron 26 accumulation in the channel and increase d conductivity for larger drain current.

Figure 19:
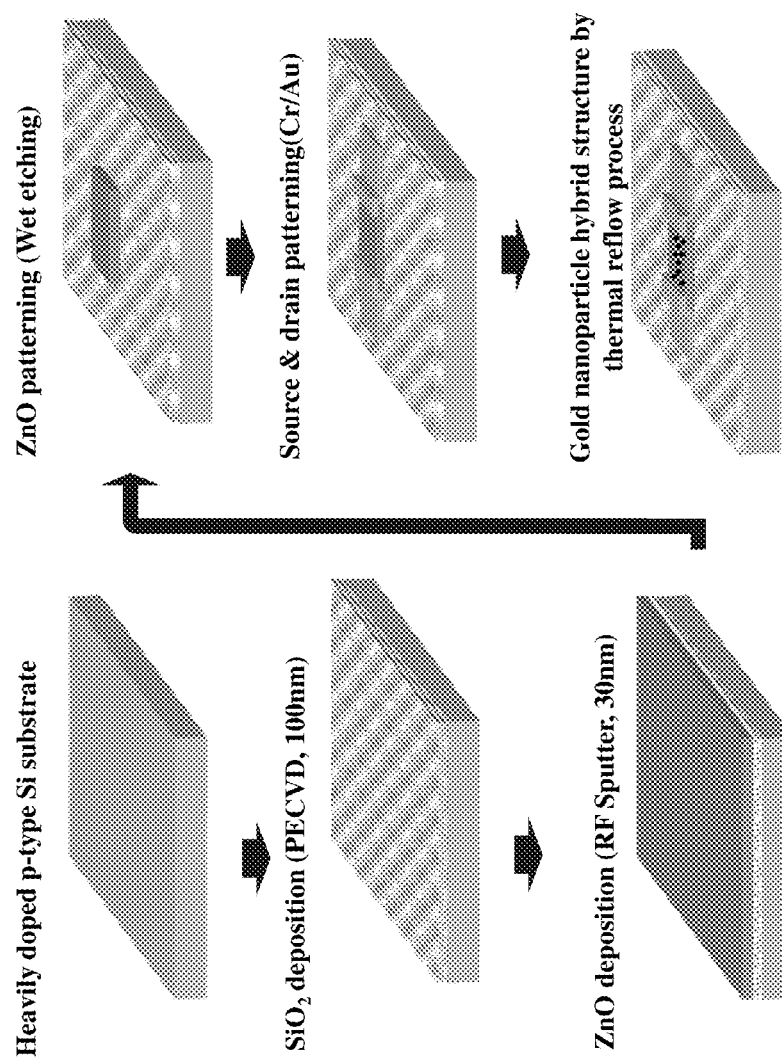
FIG. 19 illustrates the fabrication process flow for the ZnO FET structure in accordance with the principles of the present invention.

FIG. 19 illustrates the fabrication process flow for ZnO FET 10 structure. First, a heavily doped n-type silicon substrate, i.e., material layer 16, was prepared, followed by 100 nm SiO2 film 14 deposition on top of the Si substrate 16 using a thermal oxidation process to create a dielectric layer for Gate bias. A thin n-type ZnO film 12 (30, 50 and 100 nm thickness) was then deposited using RF sputter machine to create an active semiconductor channel of FET 10. Ar ambient was maintained at 5 mTorr pressure in the chamber and the substrate temperature was controlled to maintain 250° C. while the deposition process was carried out at 300 W RF source power.

Figure 20:
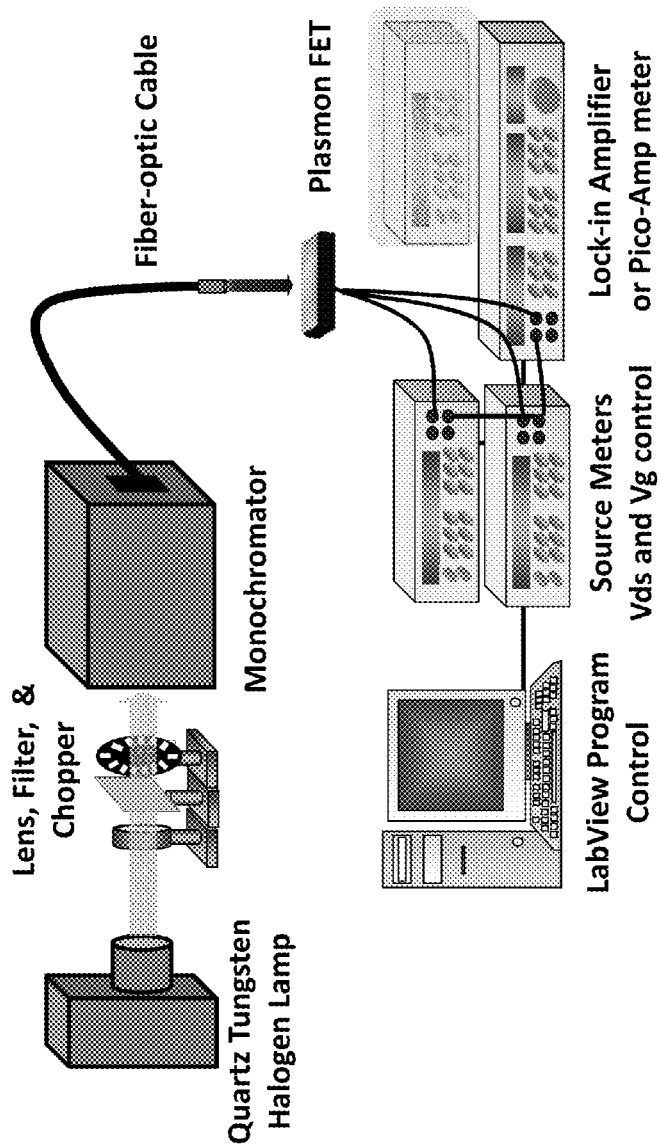
FIG. 20 illustrates a setup for testing the FET in accordance with the principles of the present invention.

The deposition rate was modulated to be 7.3 nm/min, while the substrate was rotated for uniformity. Then, the ZnO layer 12 was patterned using typical photolithography and wet etching processes. To create Drain and Source electrode 18 contacts to the n-type ZnO film 12, Cr/Au layers were deposited on the photoresist patterned substrate using an electron beam evaporator. After the lift-off process, the device becomes a fully functional field effect transistor (FET 10). Finally, gold nanoparticles 20 were added on top of the ZnO channel using a thermal reflow method to create a self-assembled gold nanoparticle 20 structure on the ZnO surface 12. Several reflow conditions were tested to control the narrow size distribution and optimize the spherical shape of gold nanoparticles, e.g., a 5 nm thin gold film with 320° C. of heat treatment for 10 minutes was used. The dimensions of the fabricated devices ranged from 10 μm to 100 μm for channel length (L) and width (W). The gold nanoparticle structure on the ZnO channel layer is also shown in FIG. 2. FIG. 20 illustrates a setup for testing FET 10 including applying one or more bias voltages and detecting plasmon induced current.

Figure 21:
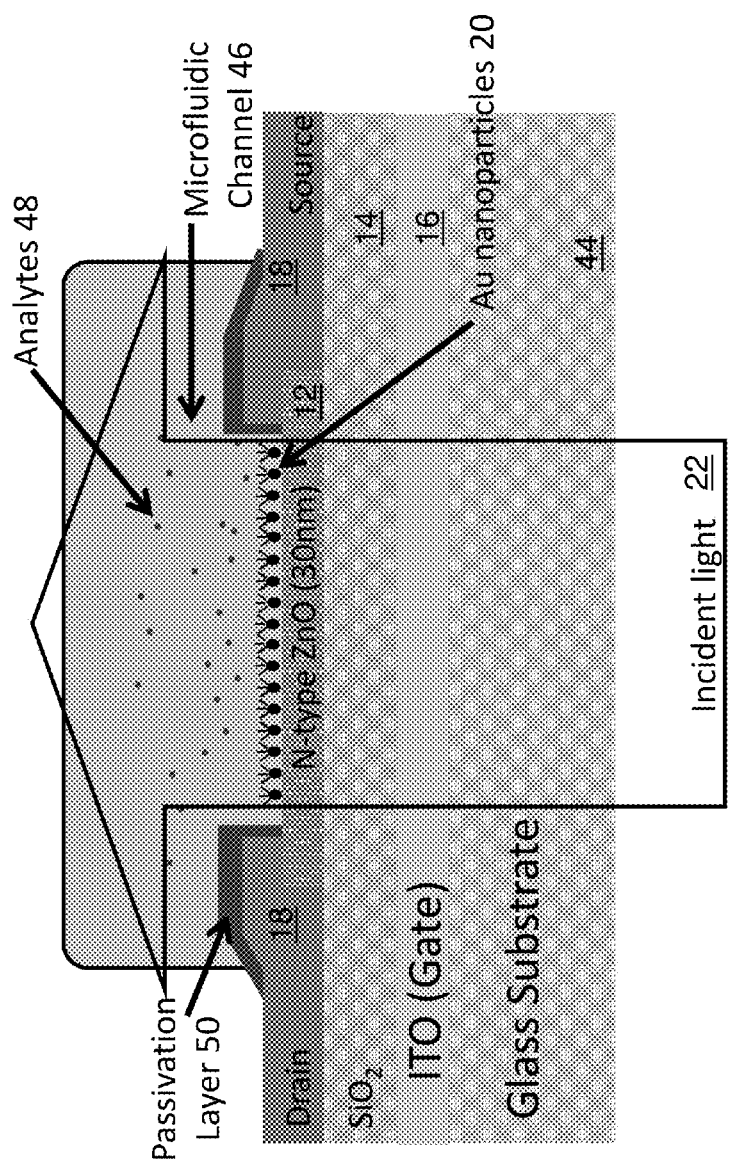
FIG. 21 illustrates another embodiment of the FET in accordance with the principles of the present invention.

FIG. 21 illustrates another embodiment of FET 10 in accordance with the principles of the present invention in which FET 10 is a biosensing device. Light illumination from bottom of the biosensing device will enable the biosensing device to avoid non-necessary absorption in the liquid sample and integration in the micro fluidic channel. Based on the property of plasmon resonance frequency shift by changing refractive index surrounding nanoparticle, FET 10 of FIG. 21 is a highly sensitive bio or chemical sensor. As shown in FIG. 21, the excitation light can delivered through the glass substrate. This configuration prevents absorption from the liquid (serum, blood etc.) in the microfluidic channel. Therefore, the optical response from the nanoparticles can be detected as same as the light illumination from above. The gold nanoparticles 20 can be functionalized for any specific target molecules using proteins, antibody and other chemicals. The average refractive index surrounding nanoparticle 20 will be higher when the targeted analytes are attached on the surface. This results to a red shift of absorption spectrum and finally variation of drain current of FET 10. Since the plasmonic absorption is not dependent to the incident angle to the nanoparticles, the entire sensing device with FET 10 can be rugged into extremely small volume (less than 1 mm$^3$). Therefore, FET 10 can detect specific analytes in this configuration.

Figure 22:
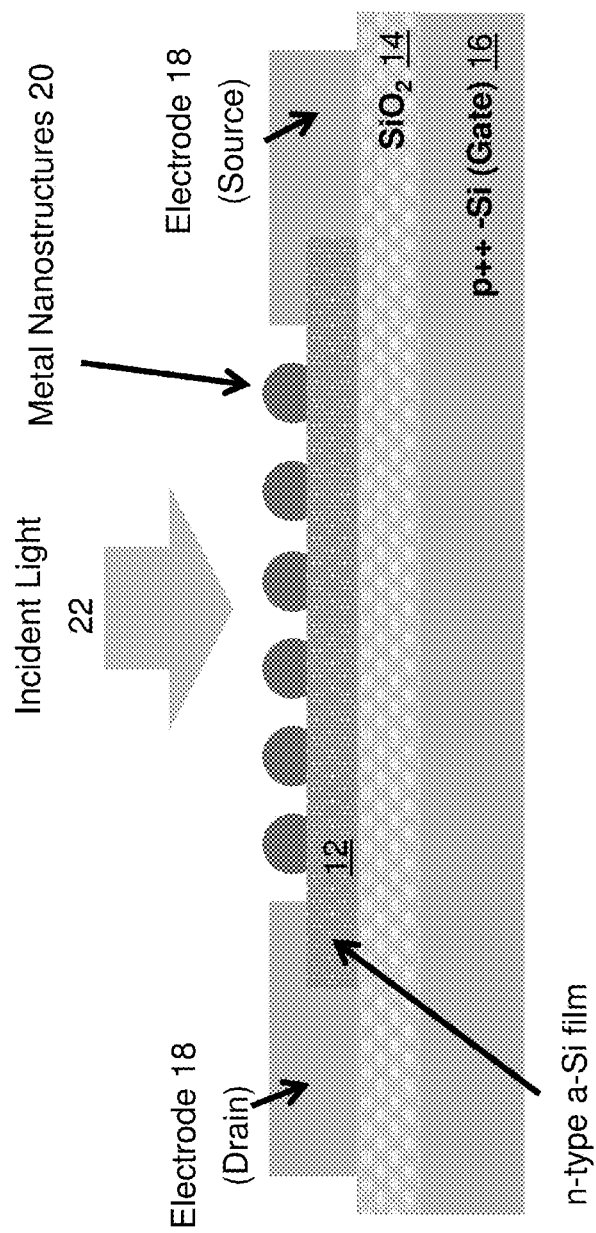
FIGS. 22-23 illustrate another embodiment of the FET in accordance with the principles of the present invention.
Figure 23:
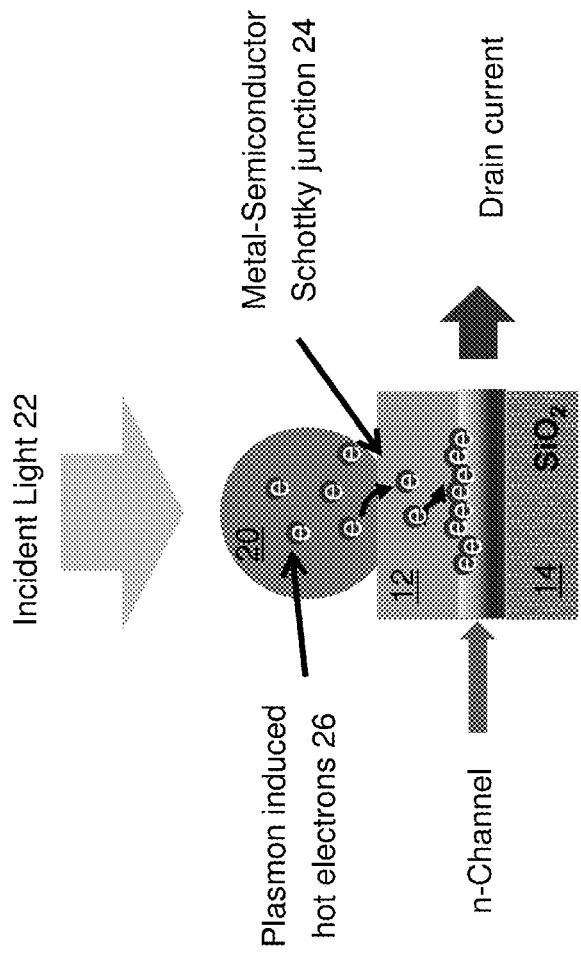
Figure 24:
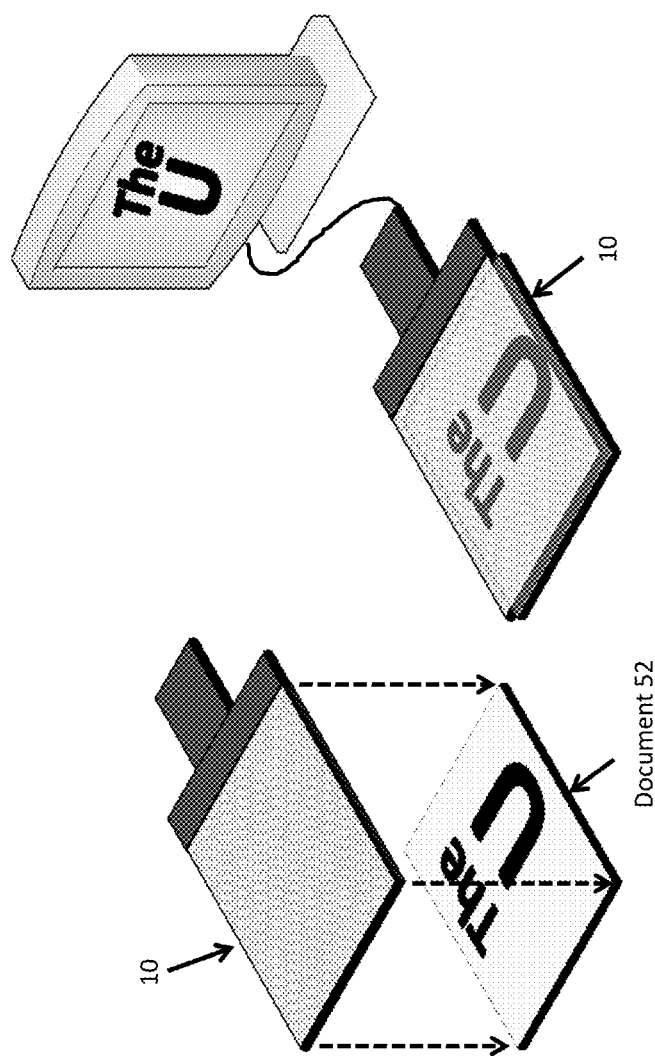
FIG. 24 illustrates another embodiment in accordance with the principles of the present invention.

FIG. 22-23 illustrates another embodiment in which first material layer 12 is a n-type a-Si film. Similar to FIGS. 2-3, plasmon induced hot electrons 26 move to the first material layer 12. FIG. 24 is another embodiment in accordance with the principles of the present invention in which a transparent plasmon FET 10 is used as an imaging device to image document 52. Because plasmonic FET 10 is fabricated on a transparent substrates (such as glass or quartz), it has a detection capability as well as transparency. This feature enables a transparent imaging device that can image with a contact to a document surface and just ambient light source.

Figure 25:
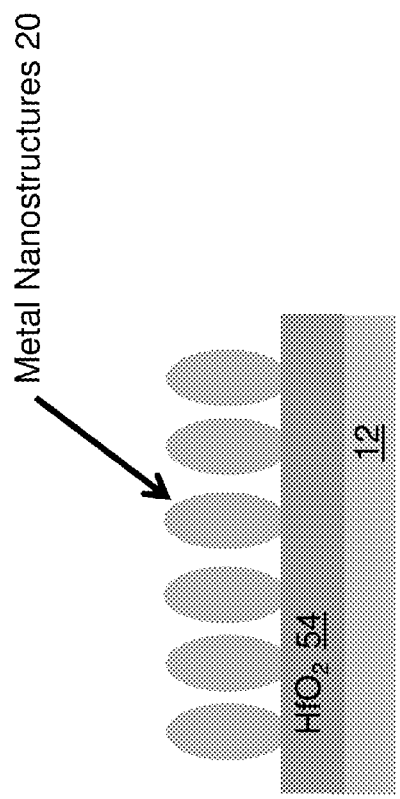
FIG. 25 illustrates another embodiment of the FET in accordance with the principles of the present invention.

FIG. 25 illustrates the HfO$_2$ layer 54 that is disposed between the plurality of nanostructures 20 and first material layer 12, e.g., ZnO layer. The additional Hafnium oxide (HfO$_2$) layer 54 may be added to other embodiment discussed above in accordance with the principles of the present invention. Other material(s) and/or compounds other than HfO$_2$ may be used in accordance with the principles of the present invention.

Figure 26:
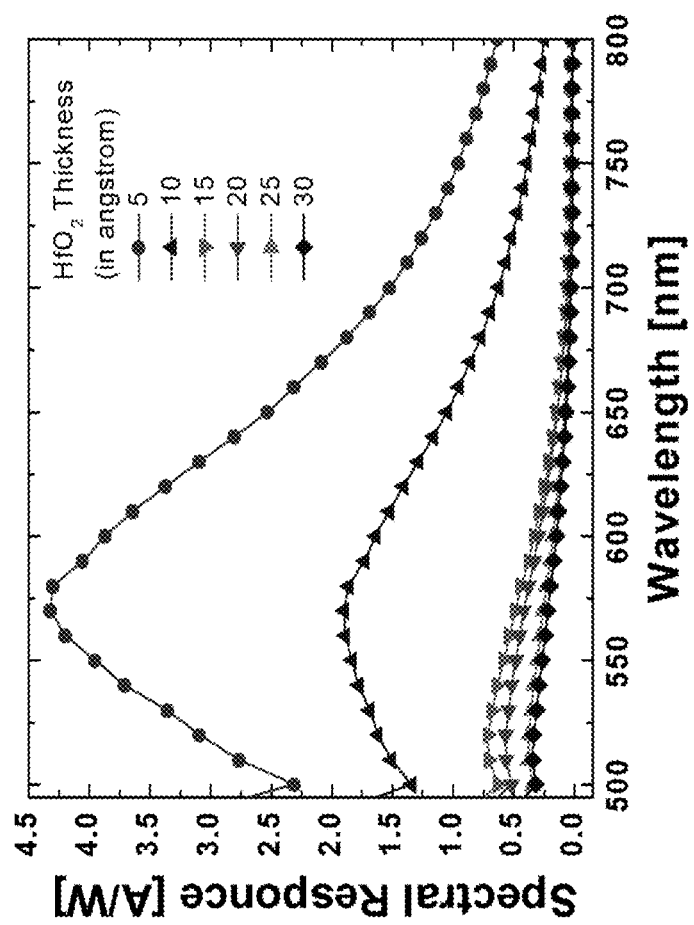
FIGS. 26-27 illustrate the spectral response of the FET of FIG. 25 in accordance with the principles of the present invention.
Figure 27:
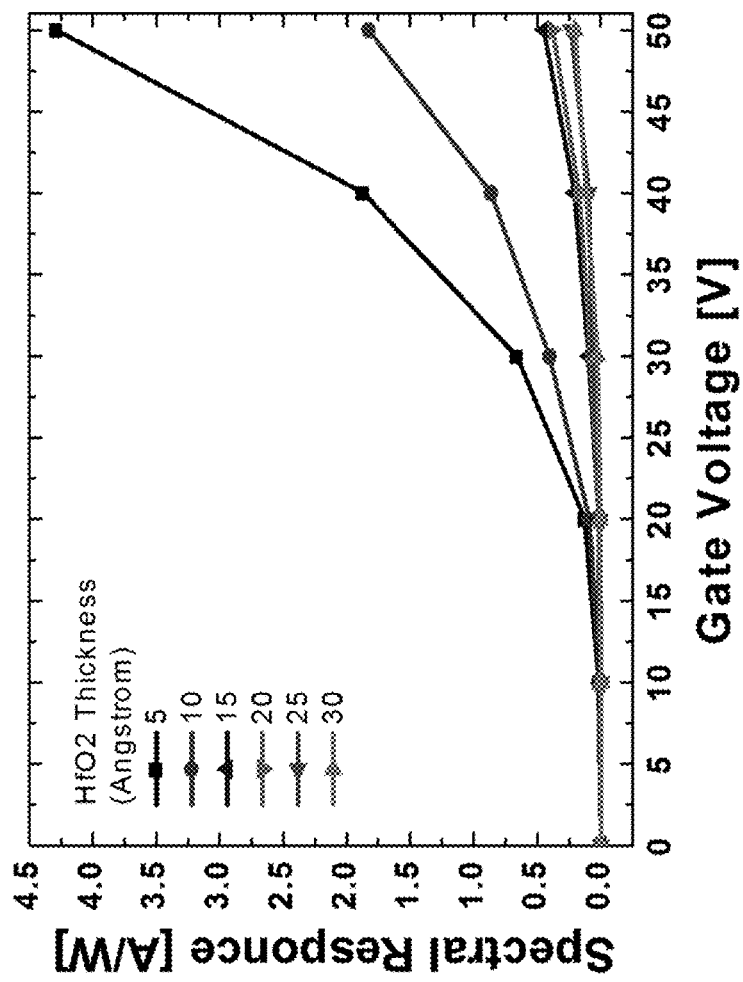

FIGS. 26-27 illustrates the spectral response of FET 10 illustrate din FIG. 25. In particular, HfO$_2$ layer (5-30 Å) is inserted in FET 10 at the Schottky boundary (between gold nanoparticles 20 and ZnO layer 12, the HfO$_2$ layer 54 is disposed on first material layer 12 and nanostructures 20 are disposed on the HfO$_2$ layer). The spectral responses under 50V gate voltage bias is illustrated in FIG. 26. The peak positions are shifted due to the size difference of gold nanoparticles 20 and change of refractive index due to HfO$_2$ layer, i.e., higher refractive index of HfO$_2$ and ZnO layers. Spectral response at the peak position in each spectrum under different gate voltage bias is illustrated in FIG. 27. Since the HfO2 is an insulating layer, the different thicknesses may be used as the strength of gate voltage bias. The probability of quantum tunneling is an exponential function (T=e$^{-\infty L}$, where, T is the probability of tunneled electrons, a is relative coefficient and L is the wall length).

As shown in FIGS. 26-27, the drain current is decreased exponentially when the wall thickness is increased that matches the expectation of tunneling induced hot electron migration, thereby confirming that quantum tunneling is one of the mechanisms of hot electron migration from the nanostructures to the semiconductor channel. In addition, the strong electric field creates a force to drift the hot electrons to the channel area of FET 10. The migrated hot electrons increase the carrier concentration in the channel of FET 10, resulting in higher channel conductivity. These synergetic processes in FET 10 enable highly efficient spectral response.

FET 10's gate bias controlled hot-electron emission and current control enables efficient hot-electron extraction absorption by localized plasmon resonance. Strong drift field in the channel and tunneling structure in FET 10 enables high photo responsivity. A transparent imaging device or a broad band (UV-IR) optical detector can be used by selecting different metal-Schottky junction material in accordance with the principles of the present invention. FET 10 plasmon sensor has several advantages over convention sensors such as extremely small size for integration and multiplexing, no need of complex optical geometry and robust operation.

FET 10 provides numerous advantages over existing devices. For example, FET 10 has strong plasmonic absorption from metal nanoparticle, highly sensitive SPR sensor and transparent imaging device. Further, FET 10's submicron device size with Surface Plasmon based function enables an integrated chip level SPR sensor. FET 10 also has a tunable absorption spectrum using controlled refractive index covered metal nanoparticle, e.g., immerse nanoparticles in an aqueous solution, and has a wide spectral response. In detector applications, FET 10's wide spectrum and IR capabilities can be customized based on the teaching, herein, by changing type of nanoparticle and the refractive index. Further, FET 10 allows nanostructures 20, e.g., gold nanoparticles, to be electrically isolated from drain, source and gate electrodes.

FET 10 may operate at room temperate at more than 1 Mhz of sensor detection speed, up to the THz frequency range for military and security applications. Further, FET 10 provide a plasmonic bridge device that can be integrated with conventional electronics on the same substrate. Further, FET 10 has good thermal stability as an IR detector at room temperature since FET 10 does not rely on the semiconductor bandgap to absorb photons. Therefore, the effect from the temperature induced free carrier is not critical in detection of low energy photons.

First material layer 12, second material layer 14 and third material layer are not limited to specific materials and/or compounds described herein, and may include one or more other materials and/or compounds that allow FET to detect electromagnetic energy through plasmonic absorption.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A plasmon field effect transistor (FET), the plasmon FET comprising:
    a n-type semiconducting layer;
    a source electrode disposed at least in part on the n-type semiconducting layer;
    a drain electrode disposed at least in part on the n-type semiconducting layer;
    a gate electrode;
    a dielectric layer disposed between the n-type semiconducting layer and the gate electrode, the gate electrode configured to provide voltage controlled amplification when a voltage is applied to the gate electrode;
    a plurality of plasmonic nanostructures disposed on the n-type semiconducting layer and being electrically isolated from both the source electrode and drain electrode, the plurality of plasmonic nanostructures configured to provide plasmonic absorption of photons and affect a drain current of the plasmon FET based at least in part on the plasmonic absorption of photons.

2. The plasmon FET of claim 1, wherein the n-type semiconducting layer creates an electron channel in the plasmon FET;

the plurality of plasmonic nanostructures are a plurality of metal plasmonic nanostructures including one of gold, silver, copper, doped metal oxide and tungsten.

3. The plasmon FET of claim 1, wherein the plurality of plasmonic nanoparticles and the n-type semiconducting layer form a Schottky Junction that allows only plasmonic hot electron transfer from the plurality of plasmonic nanoparticles to the n-type semiconducting layer.

4. The plasmon FET of claim 1, wherein the n-type semiconducting layer is one of a Si layer and semiconducting metal oxide layer.

5. The plasmon FET of claim 1, wherein the plurality of plasmonic nanostructures are not in direct contact with the source, drain and gate electrodes.

6. The plasmon FET of claim 1, wherein the plasmonic absorption of photons creates a plurality of plasmonic hot electrons that are configured to at least one of diffuse and tunnel into the n-type semiconducting layer to increase the drain current.

7. The plasmon FET of claim 1, wherein the plurality of the plasmonic nanostructures are configured to exhibit a plasmon absorption spectrum in a wavelength range between 300 nm to 100 µm.

8. The plasmon FET of claim 1, wherein the gate electrode is configured to create a current channel in the n-type semiconducting layer and facilitate hot electron transfer at a Schottky Junction when the voltage is applied to the gate electrode;
the Schottky junction being formed by the plurality of plasmonic nanoparticles and the n-type semiconducting layer; and
the hot electron transfer configured to increase the drain current.

9. The plasmon FET of claim 8, wherein the voltage applied to the gate electrode is positive;
the current channel in the n-type semiconductor layer configured to provide electron tunneling from the plurality of plasmonic nanoparticles to the n-type semiconducting layer when photons are absorbed by the plurality of plasmonic nanoparticles.

10. The plasmon FET of claim 1, wherein the plurality of plasmonic nanostructures are configured to modify an optical response of the FET.

11. The plasmon FET of claim 1, wherein the plurality of plasmonic nanostructures are at least partially coated by the n-type semiconducting layer, the at least partial coating is configured to shift a wavelength of plasmonic absorption of the FET to one of a shorter and longer wavelength.

12. A sensor device, the sensor device comprising:
a n-type semiconducting layer;
a source electrode disposed at least in part on the n-type semiconducting layer;
a drain electrode disposed at least in part on the n-type semiconducting layer;
a gate electrode;
a dielectric layer disposed between the n-type semiconducting layer and the gate electrode, the gate electrode configured to provide voltage controlled amplification when a voltage is applied to the gate electrode;
a plurality of plasmonic nanostructures disposed on the n-type semiconducting layer and being electrically isolated from both the source electrode and drain electrode, the plurality of plasmonic nanostructures configured to provide plasmonic absorption of photons and affect a drain current of the plasmon FET based at least in part on the plasmonic absorption of photons; and
a current detector, the current detector configured to detect an increase in the drain current of the plasmon FET when light of at least one wavelength is incident on the plurality of plasmonic nanostructures, at least one bias voltage of the source electrode and drain electrode remaining unchanged during the detected increase of the drain current.

13. The sensor device of claim 12, wherein the n-type semiconducting layer creates an electron channel in the FET;
the plurality of plasmonic nanostructures are a plurality of metal plasmonic nanostructures including one of gold, silver, copper, doped metal oxide and tungsten.

14. The sensor device of claim 12, wherein the plurality of plasmonic nanoparticles and the n-type semiconducting layer form a Schottky Junction that allows only plasmonic hot electron transfer from the plasmonic nanoparticle to the n-type semiconducting layer.

15. The sensor device of claim 12, wherein the n-type semiconducting layer is one of a Si layer and semiconducting metal oxide layer.

16. The sensor device of claim 12, wherein the plurality of plasmonic nanostructures are not in direct contact with the source, drain and gate electrodes.

17. The sensor device of claim 12, wherein the plasmonic absorption of photons creates a plurality of plasmonic hot electrons that are configured to at least one of diffuse and tunnel into the n-type semiconducting layer to increase the drain current.

18. The sensor device of claim 12, wherein the gate electrode is configured to create a current channel in the n-type semiconducting layer and facilitate hot electron transfer at a Schottky Junction when the voltage is applied to the gate electrode;
the Schottky junction being formed by the plurality of plasmonic nanoparticles and the n-type semiconducting layer; and
the hot electron transfer configured to increase the drain current.

19. The sensor device of claim 18, wherein the barrier thickness of the Schottky junction is reduced when the voltage applied to the gate electrode is positive, the reduced barrier thickness is configured to provide electron tunneling from the plurality of plasmonic nanoparticles to the n-type semiconducting layer when photons are absorbed by the plurality of plasmonic nanoparticles.

20. A plasmon field effect transistor (FET), the plasmon FET comprising:
a first material layer, the first material layer being an n-type semiconducting layer;
a second material layer, the second material layer being a dielectric layer including one of a Silicon Dioxide ($SiO_2$) layer, Silicon Nitride ($SiN_x$) layer and Aluminum Oxide ($Al_2O_3$) layer; and
a third material layer, the third material layer including a p-type silicon substrate layer and a gate electrode, the gate electrode configured to provide voltage controlled amplification when a voltage is applied to the gate electrode, the second material layer being disposed between the n-type semiconducting layer and the gate electrode;
a source electrode disposed at least in part on the n-type semiconducting layer;
a drain electrode disposed at least in part on the n-type semiconducting layer; and
a plurality of gold plasmonic nanostructures disposed on the first material layer, the plurality of gold plasmonic nanostructures being electrically isolated from the source electrode, drain electrode and gate electrode, the plurality of gold plasmonic nanostructures configured to provide plasmonic absorption of photons and contribute to a drain current of the FET based at least in part on the plasmonic absorption of photons.

* * * * *